United States Patent
Klett-Loch

(10) Patent No.: US 6,458,761 B2
(45) Date of Patent: Oct. 1, 2002

(54) SYNTHETIC, STATISTIC THYMIC PEPTIDE COMBINATION AND ITS USE AS A PREPARATION WITH IMMUNOLOGICAL AND/OR ENDOCRINOLOGICAL EFFECT

(76) Inventor: Lore Maria Klett-Loch, Bautzener Weg 1-3, D-68309 Mannheim (DE)

( * ) Notice: Subject to any disclaimer, the term of this patent is extended or adjusted under 35 U.S.C. 154(b) by 0 days.

(21) Appl. No.: 09/766,686

(22) Filed: Jan. 22, 2001

Related U.S. Application Data

(63) Continuation of application No. 09/424,625, filed as application No. PCT/DE97/01061 on May 26, 1997, now abandoned.

(51) Int. Cl.⁷ .............. A23L 1/305; A61K 7/00; A61K 38/00; A61K 38/17; A61P 37/04
(52) U.S. Cl. .............. 514/2; 424/439; 424/580; 426/657; 514/21; 530/300; 530/333; 930/180
(58) Field of Search .............. 424/61, 69, 70.1, 424/401, 439, 580; 426/657; 435/68.1; 514/2, 8, 12, 21; 530/300, 301, 333, 343; 930/180

(56) References Cited

U.S. PATENT DOCUMENTS

| | | | |
|---|---|---|---|
| 4,500,450 A | 2/1985 | Seipke et al. | 530/300 |
| 4,826,680 A | 5/1989 | Jaegger | 514/21 |
| 5,521,164 A | 5/1996 | della Valle et al. | 514/54 |

FOREIGN PATENT DOCUMENTS

| | | |
|---|---|---|
| EP | 0 237 398 A | 9/1987 |
| WO | WO 96 17584 A | 6/1996 |

OTHER PUBLICATIONS

Translation of "Process For The Preparation . . . ", Redzinsale et al, EP Patent Application 237,398, Sep. 16, 1987.*

Cordero et al., "Novel Approaches to Immunotherapy Using Thymic Peptides," *Immunology Today*, Jan. 1997, pp. 10–13, vol. 18, No. 1, XP004016755.

Lee et al., "The Assay Development of a Molecular Marker for Transmissible Spongiform Encephalopathies," *Electrophoreses 1997*, pp. 502–506, vol. 18.

Maybeck et al., Abstract of European Patent Application 237,378, *West*, Sep. 16, 1987.

* cited by examiner

*Primary Examiner*—Jeffrey E. Russel
(74) *Attorney, Agent, or Firm*—Alston & Bird LLP

(57) ABSTRACT

Immunologically and/or endocrinologically active preparation containing as an active ingredient short-chain peptides with a weighted quantity ratio and a pattern of amino acids characteristic of thymus tissue.

14 Claims, 4 Drawing Sheets

Mitogenic costimulation/determination of the cell proliferation rate (incorporation of ³H-thymidine), donor KFG, PHA concentration of 0.05 μg/ml ated June 1, 2024, by the expiration 0 days. No terms disclaimer.

SYNTHETIC, STATISTIC THYMIC PEPTIDE COMBINATION AND ITS USE AS A PREPARATION WITH IMMUNOLOGICAL AND/OR ENDOCRINOLOGICAL EFFECT

CROSS-REFERENCE TO RELATED APPLICATIONS

This application is a continuation of U.S. application Ser. No. 09/424,625, filed Nov. 24, 1999, now abandoned which is a U.S. National Phase application of PCT/DE97/01061, filed May 26, 1997. The contents of the above applications are incorporated herein by reference in their entirety.

FIELD OF THE INVENTION

The invention relates to a synthetic, statistic thymic peptide combination and its use as an immunologically and endocrinologically active preparation.

BACKGROUND OF THE INVENTION

From an increasing number of scientific publications, it becomes obvious that a communication exists by means of low-molecular signaling substances between the brain, the organs of the immune system (bone marrow, thymus, lymph nodes, spleen, intestinal mucosa, pulmonary epithelium, and body skin) and the endocrine system of the hormonal control. From the thymic tissue, low-molecular proteins, so-called signaling peptides, were identified, which function both on a neuronal level as neurotransmitters and on an immunological level as differentiation factors.

It was possible to prove in animal experiments that low-molecular signaling peptides are capable of inducing a differentiation cascade in T and B lymphocytes from pluripotent parent cells, when such active peptide substances are subcutaneously supplied to the organism. Moreover, is has been found that such signaling molecules, whose composition corresponds to the proteinic elements of the thymus gland, are capable of protecting the organism against opportunistic infections, when same has previously been harmed, for example, by X-rays, cancer chemotherapy, or a latent virus infection. Such early damage to the regulatory equilibrium of the organism is accompanied by hormonal disorders, which express themselves by changed fertility, reduced mental and physical performance, sleep disorders, and loss of appetite. Moreover, humans exhibit a reduced protective function of the skin as well of the quality of hair and nail growth.

From experience, medical science has countered this syndrome for a long time in that preparations of organic extracts are used as medicines or food supplements. Such preparations of the thymic tissue from animals, in particular thymus of the calf, have found wide use, even when a molecularly defined principle of action of such preparations has not been described until now. Positive data from a series of biological studies in vivo with such thymus preparations permit concluding that substances contained in the thymus tissue exert synergistic effects both on the neuronal and on the immune system. However, in the last five years the risk has come to the fore that such preparations of organic extracts from animals are contaminated with prion proteins. These prion proteins are associated with transmitting the symptoms of BSE (bovine spongiform encephalopathy, "bovine madness").

It is therefore the object of the present invention to make available an immunologically and/or endocrinologically active preparation, which permits on the one hand extrapolating the positive experience with thymic peptide combinations, but totally excludes on the other hand the risk of BSE. Furthermore, it is the object to specify a synthetic, statistic thymic peptide combination and its use as an immunologically and/or endocrinologically active preparation with corresponding advantages.

SUMMARY OF THE INVENTION

The invention provides synthetic thymic peptide combinations in the absence of risk of BSE by synthetically building the peptides characteristic of thymus from chromatographically clarified amino acids. An immunologically and endocrinologically active preparation can be prepared that contains as an active ingredient short-chain peptides characteristic of thymic tissue.

Methods for preparing the synthetic thymus peptide combinations are also provided. These methods include the synthesis of peptides from chemically suitable derivated amino acids while maintaining the weighted quantity ratio and pattern of amino acids characteristics of the thymus tissue. The amino acids are activated for a sequence of reactions in which one active N-terminal group is alternately protected and then deprotected until the discrete peptide sequence is built. Preparations of calf thymus extract obtained by partial hydrolysis of the thymus tissue have been commercially available. In sharp contrast thereto, the synthetic thymus peptides of the invention are prepared by separating the amino acids; functionalizing the amino acids for peptide buliding reactions; reacting the amino acids to build a peptide combination by alternately reacting the amino acids to join them together in a weight ratio characteristics of thymus tissue, deprotecting a remaining reactive group, and again reacting the amino acids to continue building the peptide to the desired products, whereby prions are excluded.

The preparations of the invention, which are synthetic, statistic thymic peptides having a weighted quantity ratio and pattern of amino acids characteristic of thymus tissue and having immunologically and endocrinologically active properties, can be used to treat weak immunity and immunodeficiencies and hormonal disorders, and can be used in the cosmetic field as a nutrient for skin, hair, and nails, and as a dietary supplement in the field of food supplements.

Proceeding from partial hydrolysates of thymic protein, protein mixtures from short-chain thymic peptides and amino acids, which result from an enzymatic and/or chemical partial hydrolysis of thymus tissue, such combinations were clarified by way of chromatography and amino-acid analysis to that extent that the such partial hydrolysates consist of short-chain peptides with a quantity ratio and pattern of amino acid characteristic of thymus tissue. When such amino acids are reacted with one another in chemically suitably derivatized form, with the quantity ratio of the amino acids characteristic of the thymus tissue being maintained, when such synthetic combinations are released from their N-terminal protective groups and coupled again and repeatedly with such weighted combinations of amino acids, which are characteristic of thymus tissues, one will obtain synthetic, statistic thymic peptide combinations to the total exclusion of the prion protein risk.

Thus, the invention discloses relatively simple ways of purposefully producing immunologically and endocrinologically active preparations with an effect of the preparation that is standardizable for the first time.

It is possible to produce such thymic peptide combinations in a pharmaceutically reproducible sterile manner, so that a preparation results in this manner, which depending on the number of repeated statistic synthesis operations consists of a family of signaling thymic peptides characteristic of neurotransmitters and immunologically active signaling molecules. Based on analytical tests in comparison with partial hydrolysis mixtures from natural thymus tissue, it was possible to demonstrate that, within the margin of error of applied analytical methods, synthetic, statistic thymic peptide combinations are comparable in their composition with the natural preparation. From this follows that it was possible to accomplish the object of the present invention to eliminate the BSE risk by synthesizing a thymic peptide combination.

Surprisingly, it has shown that the synthetic preparation of the present invention exhibits in the biological test on human lymphocytes a superior activity with respect to mitogenic co-stimulation (induction of cell proliferation) in comparison with a commercial thymic preparation produced by partial hydrolysis.

Furthermore, it comes as a surprise that the synthetic preparation is capable of binding constituents of the extracellular matrix, a property that had previously to be ascribed only to scleroproteins.

BRIEF DESCRIPTION OF THE DRAWINGS

Figure 1:
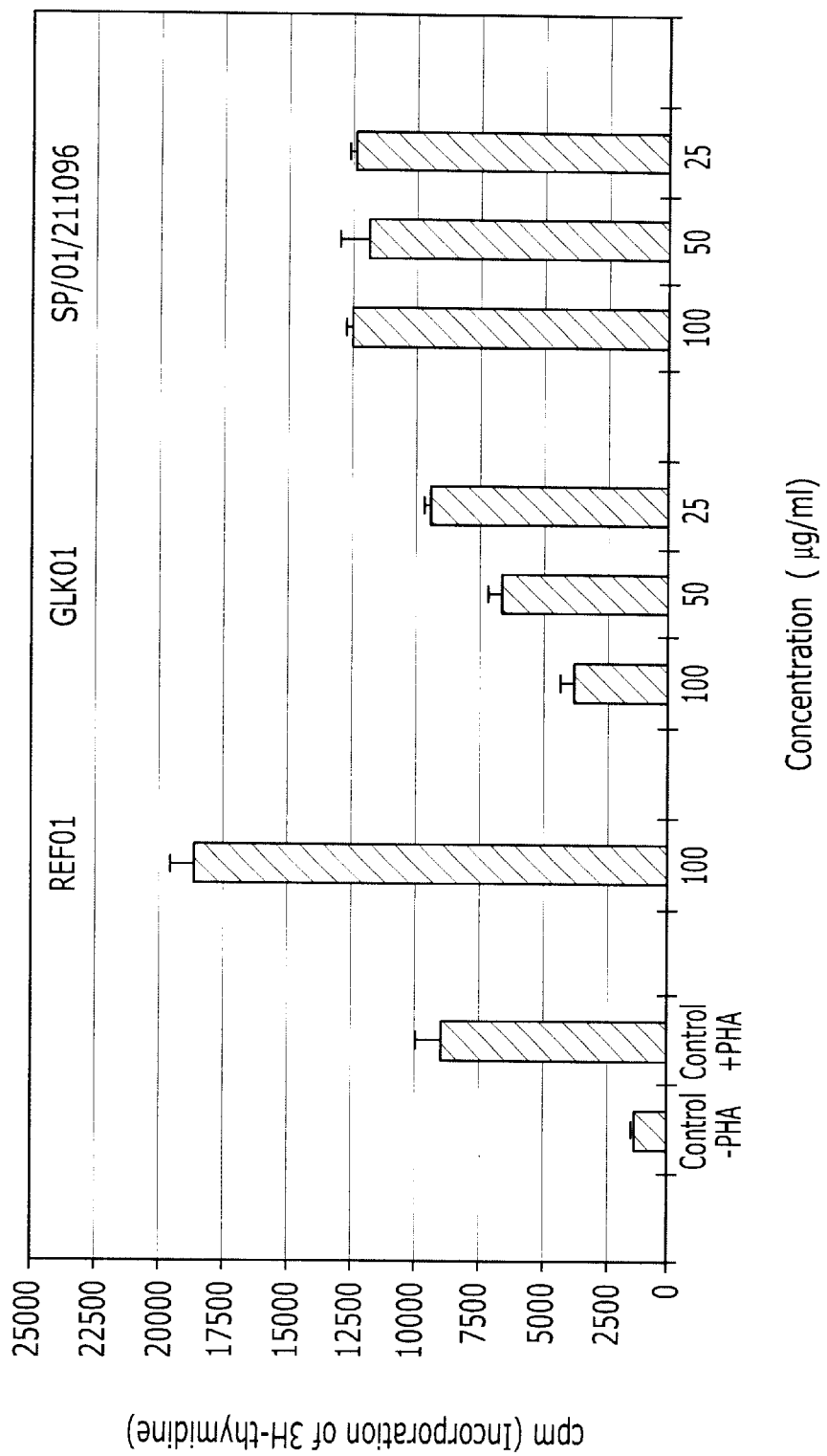

Having thus described the invention in general terms, reference will now be made to the accompanying drawings, which are not necessarily drawn to scale, and wherein:

FIG. 1 is a graphic representation of data from the mitogenic co-stimulation of human peripheral blood lymphocytes (PBL's) obtained from a first donor with phytohemagglutinin (PHA) in the presence of a positive control (REF01), a commercial thymic peptide combination (GKL01) and the statistic thymic peptide combination (SP/01/211096).

Figure 2:
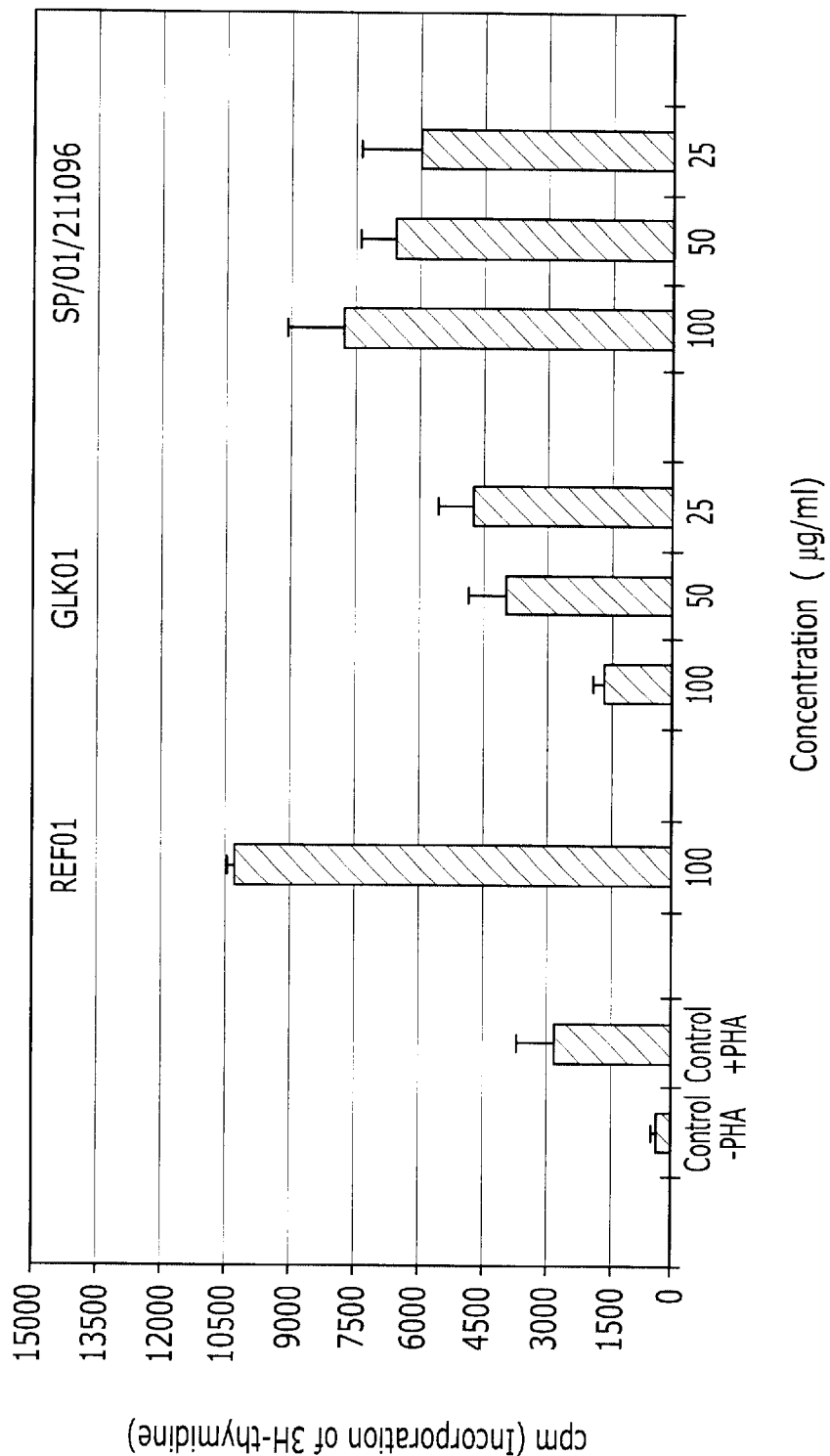

FIG. 2 is a graphic representation of data from the mitogenic co-stimulation of human PBLs obtained from a second donor with PHA in the presence of a positive control (REF01), a commercial thymic peptide combination (GKL01) and the statistic thymic peptide combination (SP/01/211096).

Figure 3:
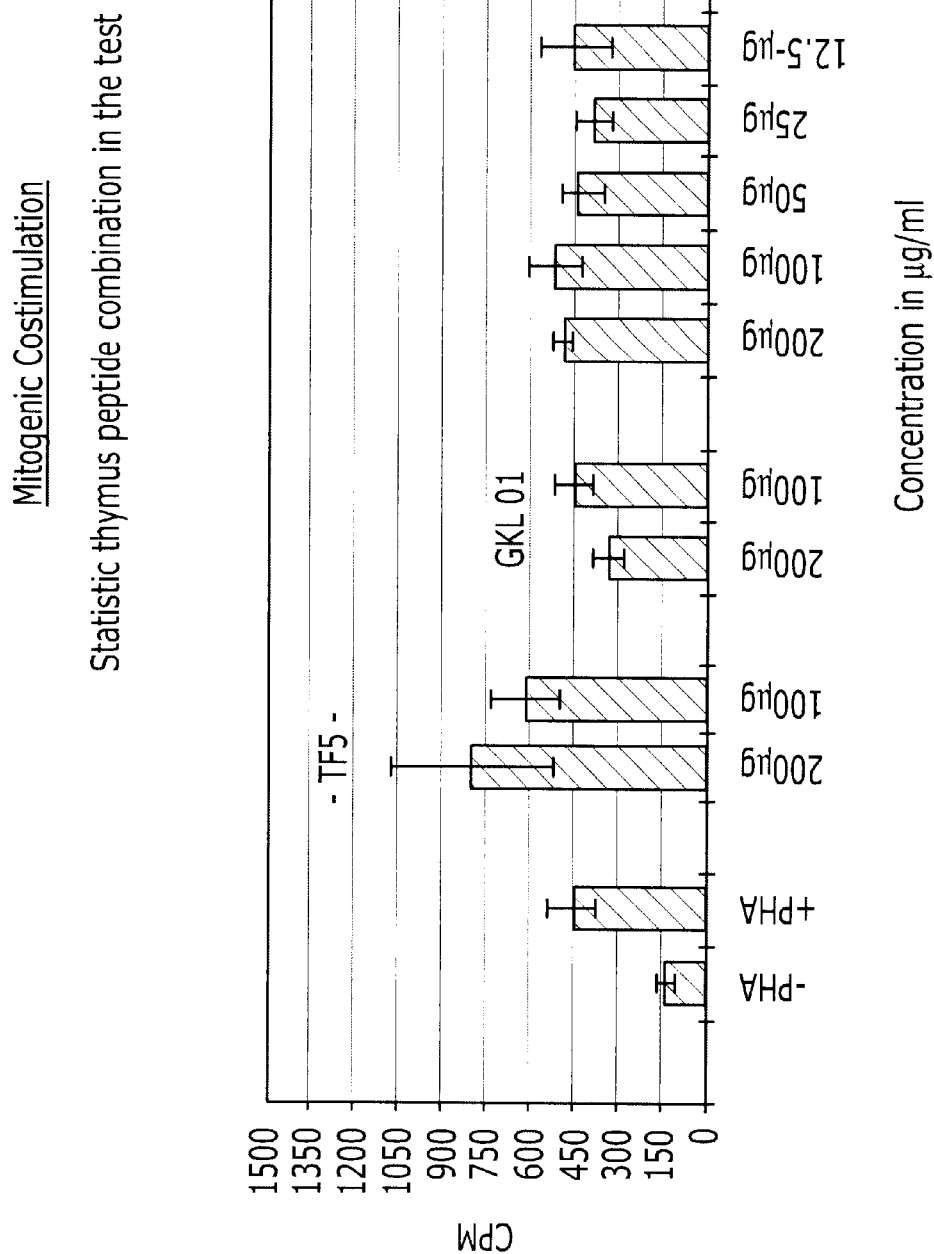

FIG. 3 is a graphic representation of data from the mitogenic co-stimulation of human PBLs obtained from a third donor with PHA in the presence of a positive control thymosin fraction 5 (TF5), a commercial thymic peptide combination (GKL01) and the statistic thymic peptide combination (SP/01/211096).

Figure 4:
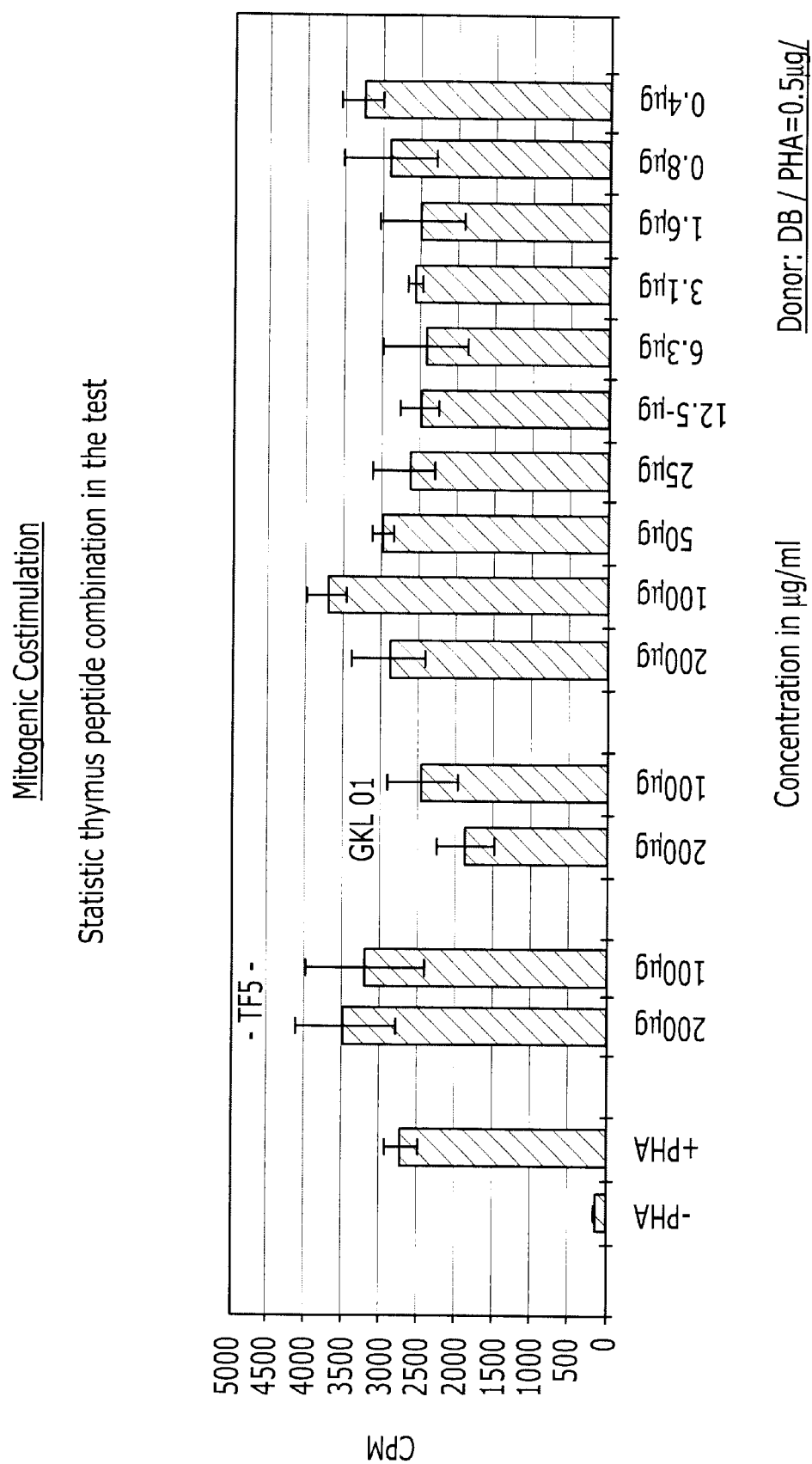

FIG. 4 is a graphic representation of data from a second mitogenic co-stimulation of human PBLs obtained from the third donor with PHA in the presence of a positive control thymosin fraction 5 (TF5), a commercial thymic peptide combination (GKL01) and the statistic thymic peptide combination (SP/01/211096).

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention is described in greater detail with reference to the following examples.

EXAMPLE 1

The statistic thymic peptide combinations of the present invention were examined for bioactivity in the test system of the mitogenic co-stimulation in comparison with a commercial thymic preparation from partial hydrolysis. Tested were end concentrations of 100, 50, and 25 µg/ml.

In the case of two donors (KFG and WH) the statistic thymic peptide combination shows a statistically significantly higher bioactivity than a commercial thymic preparation from partial hydrolysis. While at the high concentration of 100 µg/ml, an inhibition of cell proliferation was observed for a commercial thymic preparation from partial hydrolysis, the statistic thymic peptide combination led to a dose-dependent increase in the proliferation of human lymphocytes.

From two blood donations, human peripheral blood lymphocytes were isolated, and the proliferation rate of these cells was measured, after a suboptimal prestimulation (0.5 µg/ml phytohemagglutinin (PHA)) under the action of different concentrations of a commercial thymic preparation from partial hydrolysis, and the statistic thymic peptide combination in comparison with the positive control REF 01 (thymosin fraction 5).

In terms of the measuring technique, the proliferation rate was determined by the following method: During the active-ingredient dependent induction of the T-cell proliferation, the DNA synthesis is stimulated for purposes of cell division. Therefore, it is possible to measure via incorporation of a radioactive DNA component (3H-thymidine) the T-cell growth with reference to incorporated radioactivity.

FIGS. 1 and 2 show results from the stimulation of the blood lymphocytes of donor KFG and donor WH. The test data are to be related to the result of the control formulation after adding phytohemagglutinin (Kontr.+PHA). In the test, the reference thymus preparation was used as positive control in a concentration of 100 µg/ml; a commercial thymic preparation from partial hydrolysis and the statistic thymic peptide combination were tested in the three concentrations of 100, 50, and 25 µg/ml.

FIG. 1 shows the results for donor KFG. The reference thymus preparation used a positive control led to a very obvious increase in the proliferation rate. For a commercial thymus preparation produced by partial hydrolysis, however, it was possible to observe a dose-dependent inhibition. Only in the case of the lowest concentration of 25 µg/ml was the value of the control formulation reached. By the action of the statistic thymic peptide preparation, the cell proliferation rate was statistically significantly higher in the case of the three tested concentrations than in the control formulation.

According to FIG. 2, the lymphocytes of donor WH showed comparable results. Again, the reference thymus preparation used as positive control resulted in a considerable increase in the proliferation of human lymphocytes. A commercial thymus preparation produced by partial hydrolysis led in the concentrations of 50 and 25 µg/ml to a slight increase in the cell proliferation rate, but not in the high concentration of 100 µg/ml. However, for the statistic thymic peptide combination SP/01/211096, it was possible to observe a clear and dose-dependent increase in the DNA synthesis rate.

The object of these tests according to Example 1 was the comparative testing of the synthetic, statistic thymic peptide preparation with a commercial thymus preparation produced by partial hydrolysis in the test system of the mitogenic co-stimulation. The intent was to test the capability of the test substance of increasing the cell proliferation rate of human blood lymphocytes.

For the statistic thymic peptide combination, it was possible to find in the case of two donors a clearly higher bioactivity in comparison with the commercial thymus preparation from partial hydrolysis. In addition, donor WH showed a dose-dependent increase in the DNA synthesis rate. Surprisingly, the addition of a commercial thymus preparation from partial hydrolysis to the cell culture formulations led rather to an inhibition of the cell proliferation. Only in the case of low concentrations of 50 or 25 µg/ml was the cell proliferation rate slightly above the value of the control formulation in the case of donor WH.

EXAMPLE 2

The following example relates to the stimulation of the blood lymphocytes of donor DB. The test data are to be related with reference to FIGS. 3 and 4 to the result of the control formulation after adding phytohemagglutinin at PHA. The thymosin fraction No. 5 (TF5) was used as positive control in two concentrations (third and fourth columns from the left). For a comparison, a commercial partial thymic hydrolysate (fifth and sixth columns) was also used in the same concentration. As a control PHA was used alone.

In the mitogenic co-stimulation with suboptimal stimulation of the blood cells with PHA of 0.05 µg/ml, the synthetic-statistic thymic peptide combination shows a surprisingly distinct activity both in the case of a dose of the claimed synthesized product of 100 µg/ml/cell culture formulation and in the case of 0.4 µg/ml/cell culture formulation.

Likewise, in the case of a slight prestimulation of the blood cells with PHA in an amount of 0.025 µg/ml/formulation, one can clearly notice the effects of the synthetic-statistic thymic peptide combination according to the invention, even though less distinct than in the case of a prestimulation of the blood cells with 0.05 µg/ml PHA/formulation.

Lastly, one has in this instance a typical, in vitro, two-phase activity, which shows a maximum respectively in the range of 100 µg/ml and 0.4 µg/ml, and is in each case better than the commercial partial thymic hydrolysate that is used as comparison preparation. In any event, this two-phase activity is a proof for the wide scope of the immunological, in vitro activity, wherein the great extent of activity in the case of the extremely low concentration of 0.4 µg/ml comes no doubt as a surprise and is of great economic interest due to its really very low concentration.

The analytical data of the synthetic-statistic thymic peptide combination are as follows:

Certificate of Analysis
Data Sheet Synthetic-Statistic Thymic Peptides

| | Specifications Specified | #SP/01/211096 Found |
|---|---|---|
| Description: | yellowish powder | yellowish powder |
| Residual Solvents (GC): | <10% | |
| Water | <0.1% | 9% ± 0.5% |
| DMF | <0.1% | n.d.* < 200 ppm** |
| Methanol | <0.1% | 130 ppm < 130 ppm |
| Toluol | <0.1% | n.d. < 40 ppm |
| Ethylisopropylamine | <0.1% | n.d. < 200 ppm |
| Acetic ester | <0.1% | n.d. < 20 ppm |
| Acetates: | <3% | 1.6% ± 0.2% |
| Inorganic salts: | <0.5% | <0.2% |
| Specific rotation: (20° C. c = 0.2; H2O) | −30.0° ± 5° | −30.2° ± 0.2° |
| Free amino acid content: (%, w/w) | GKL01 ± 5% | complies |
| Total amino acid composition: (%, w/w) | GKL01 ± 5% | complies |
| Peptide content: | 50% ± 5% | complies |

What is claimed is:

1. A method for producing peptide combinations characteristic of thymus tissue comprising the steps of chromatographically separating amino acids; functionalizing the amino acids for sequential reaction to build peptides; and reacting the amino acids to produce peptide combinations characteristic of thymus tissue.

2. The method of claim 1 wherein the amino acids are derived from calf thymus.

3. The method of claim 1 wherein the step of functionalizing the amino acids for sequential reaction comprises treating the amino acids to provide N-terminal functionalities and protecting one of the functionalities from reaction.

4. The method of claim 1 wherein the step of reacting the amino acids to build peptide combinations comprises alternately reacting the amino acids to join them together, deprotecting a protected group, reacting the amino acid deprotected group, and repeating the sequence of reaction/protection/deprotection until desired peptide combinations are obtained.

5. A method for providing a standardizable, statistic, synthetic composition of thymus peptides in the absence of prion protein comprising the steps of:
   a) chromatographically separating amino acids;
   b) identifying the amino acids;
   c) chemically reacting the amino acids to provide N-terminal functionality and protecting one N-terminus from reaction;
   d) reacting the amino acids to join them together in a weight ratio and pattern characteristic of thymus;
   e) deprotecting the protected N-terminal functionality; and
   f) reacting the deprotected groups to further build a peptide in the absence of prion protein.

6. A method of promoting cellular proliferation of mammalian lymphocytes comprising contacting the mammalian lymphocytes with an effective amount of a composition comprising a synthetic peptide combination characteristic of thymus tissue.

7. A method of treating immunodeficiency to stimulate immune response comprising the step of administering an effective amount of a composition comprising a synthetic peptide combination characteristic of thymus tissue.

8. A method of treating hormone disorders comprising the step of administering an effective amount of a composition comprising a synthetic peptide combination characteristic of thymus tissue.

9. A method of treating hormone disorders comprising the step of adminstering an effective amount of a composition comprising peptide combinations produced in accordance with claim 1.

10. A method of treating immunodeficiency to stimulate immune response comprising the step of administering an effective amount of a composition comprising peptide combinations produced in accordance with claim 1.

11. A method of promoting cellular proliferatiion of mammalian lymphocytes comprising the step of contacting the mammalian lymphocytes with an effective amount of a composition comprising peptide combinations produced in accordance with claim 1.

12. A method of treating hormone disorders comprising the step of administering an effective amount of a composition comprising peptide combinations produced in accordance with claim 5.

13. A method of treating immunodeficiency to stimulate immune response comprising the step of administering an effective amount of a composition comprising peptide combinations produced in accordance with claim 5.

14. A method of promoting cellular proliferation of mammalian lymphocytes comprising the step of contacting the mammalian lymphocytes with an effective amount of a composition comprising peptide combinations produced in accordance with claim 5.

* * * * *

UNITED STATES PATENT AND TRADEMARK OFFICE
CERTIFICATE OF CORRECTION

PATENT NO. : 6,458,761 B2
DATED : October 1, 2002
INVENTOR(S) : Klett-Loch

It is certified that error appears in the above-identified patent and that said Letters Patent is hereby corrected as shown below:

Title page,
Item [56], References Cited, OTHER PUBLICATIONS,
"Redzinsale et al." should read -- Redziniak et al. --.

Column 2,
Line 11, after "thymus" insert -- tissue --;
Line 18, "derivated" should read -- derivatized --.

Column 3,
Line 14, after "has" insert -- been --.

Column 6,
Line 51, after "thymus" insert -- tissue --.

Signed and Sealed this

Twenty-eighth Day of January, 2003

JAMES E. ROGAN
*Director of the United States Patent and Trademark Office*